United States Patent
Stephens et al.

(10) Patent No.: US 8,012,698 B2
(45) Date of Patent: Sep. 6, 2011

(54) DIAGNOSTIC MARKERS OF WOUND INFECTION

(75) Inventors: Philip Stephens, Cardiff (GB); Ryan Moseley, Maesteg (GB); Rachael Clark, Skipton (GB); Breda Mary Cullen, Skipton (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 0 days.

(21) Appl. No.: 12/450,377

(22) PCT Filed: Mar. 31, 2008

(86) PCT No.: PCT/GB2008/001121
§ 371 (c)(1),
(2), (4) Date: Mar. 10, 2010

(87) PCT Pub. No.: WO2008/119974
PCT Pub. Date: Oct. 9, 2008

(65) Prior Publication Data
US 2010/0166694 A1    Jul. 1, 2010

(30) Foreign Application Priority Data
Mar. 30, 2007    (GB) .................................. 0706310.0

(51) Int. Cl.
*G01N 33/53*    (2006.01)
(52) U.S. Cl. ............................................. 435/7.1; 435/4
(58) Field of Classification Search .................. None
See application file for complete search history.

(56) References Cited

U.S. PATENT DOCUMENTS

| 2007/0053961 A1 | 3/2007 | Clark et al. |
| 2007/0053962 A1 | 3/2007 | Clark et al. |

FOREIGN PATENT DOCUMENTS

| GB | 2323166 | | 9/1998 |
| GB | 2411230 | | 8/2005 |
| GB | 2411231 | | 8/2005 |
| GB | 2415039 | | 12/2005 |
| GB | 2422664 | | 8/2006 |
| GB | 2426335 | | 11/2006 |
| GB | 2430029 | | 3/2007 |
| GB | 2430030 | | 3/2007 |
| GB | 2430031 | | 3/2007 |
| GB | 2430031 A | * | 3/2007 |
| WO | WO03040406 | | 5/2003 |
| WO | WO2004086043 | | 10/2004 |

* cited by examiner

*Primary Examiner* — Prema Mertz
(74) *Attorney, Agent, or Firm* — Morgan, Lewis & Bockius LLP (57) ABSTRACT

The present invention relates to a method of determining the microbial bioburden in a wound (in particular a diabetic ulcer) in a test subject, the method comprising the step of measuring the level of a cytokine in a wound sample, wherein a cytokine level lower than a reference level indicates a significant microbial bioburden in the wound (or a cytokine level higher than a reference level indicates an insignificant microbial bioburden in the wound). The invention provides methods of diagnosis, prognosis and treatment of wound infection, and devices and kits for use in such methods.

9 Claims, 3 Drawing Sheets

FIG. 2A

DIAGNOSTIC MARKERS OF WOUND INFECTION

STATEMENT OF RELATED APPLICATIONS

This application claims the benefit of International Application No. PCT/GB2008/001121, filed Mar. 31, 2008, which in turn claims priority to GB Application No. 0706310.0, filed Mar. 30, 2007.

All documents cited herein are incorporated by reference in their entirety.

TECHNICAL FIELD

The present invention relates to monitoring patients for the onset or development of wound infection, by determining the microbial bioburden in a wound in a test subject. The invention provides methods of diagnosis, prognosis and treatment of wound infection. The invention also provides devices and kits for use in such methods.

BACKGROUND ART

In mammals, injury triggers a complex cascade of cellular and biochemical events that result in a healed wound. Wound healing is a complex dynamic process that results in the restoration of anatomic continuity and function; an ideally healed wound is one that has returned to normal anatomic structure, function and appearance.

Chronically contaminated wounds all contain a microbial flora. These microbes may be indigenous to the patient or might be exogenous to the wound. Closure, or eventual healing of the wound is often based on a physician's ability to control the level of this microbial flora. Infection of wounds by microbes delays the healing process, since the microbes compete for nutrients and oxygen with macrophages and fibroblasts, the activities of which are essential for wound healing. Infection arises when microbes achieve dominance over the systemic and local factors of host resistance. Infection is therefore a manifestation of a disturbed host/microbe equilibrium in favour of the invading microbes. This can elicits a systemic septic response, and also inhibit the multiple processes involved in wound healing. Lastly, infection can result in a prolonged inflammatory phase and thus slow healing, or may cause further necrosis of the wound. The granulation phase of the healing process will begin only after the infection has subsided.

In clinical practice, a diagnosis of infection is often based on the presence of local pain, heat, swelling, discharge and redness, although many clinical indicators, such as inflammation and discharge, are of low predictive value of infection in wounds. The present inventors have found that these clinical indicators of infection are a poor predictor of actual, measured bacterial bioburden in wound fluids. Definitive diagnosis is achieved by microbiological analysis of wound samples. Tissue biopsy provides the most accurate results, but this is an invasive procedure that is difficult to achieve for the majority of wounds. Wound swabbing is the most common wound sampling method used in the United Kingdom, although its clinical value has been questioned. Furthermore, microbiological analysis of wound infection can take 48 to 72 hours, which allows time for infection to develop further if first-line/best-guess treatment is not employed immediately.

There therefore remains a need in the art for methods for the early diagnosis and prognosis of wound infection (elevated bacterial bioburden), and for devices and kits for use in carrying out such methods.

WO-A-03040406 describes a method of predicting or diagnosing clinical infection of a wound comprising measuring the concentration of a marker associated with an inflammatory response in wound fluid, wherein the marker is a fibronectin fragment, a neutrophil protease or a macrophage protease. An elevated level of the marker is said to correlate with increased likelihood of clinical infection. The suggested markers are: a fibronectin fragment, a neutrophil protease or a macrophage protease, for use in the manufacture of a medicament for predicting the likelihood of clinical infection of the wound or for diagnosing clinical infection of a wound. The following markers are listed: elastase, MMP-9, MMP-8, MMP-1, MMP-12 and cathepsin G. Also listed were a collagen propeptide, a collagen telopeptide, a protease inhibitor, plasmin, lactate dehydrogenase, a cathepsin, a cytokine, a peroxidase enzyme, a cortisol free radical or a growth factors. Suitably, the marker is a protease enzyme selected from the group consisting of matrix metalloproteinases (e.g. MMP-9), neutrophil elastase, plasmin, low molecular weight gelatinases and latent or active elastases, interleukin converting enzymes or tumor necrosis factor (TNFa) converting enzymes. The examples describe measuring the activity of the following markers in diabetic foot ulcer fluid: Neutrophil-derived elastase, plasmin, and matrix metalloproteinase. Elevated levels were found in wounds exhibiting signs of clinical wound infection.

WO-A-2004086043 describes a method of predicting or diagnosing clinical infection of a wound comprising measuring the concentration of a marker associated with an inflammatory response in wound fluid, where the marker is a proinflammatory cytokine. An elevated level was found to prognostic of clinical wound infection. The preferred proinflammatory cytokine is TNF-α. Further markers suggested were: Interleukins such as IL-1β, IL-4, IL-6, IL-8, IL-10, IL-18, MCP-1, MCP-2, MCP-3 (monocyte chemoattractant proteins), MIP-1α, MIP-Iβ, MIP-2 (macrophage inflammatory proteins), Interferons IFN-alpha, IFN-beta, and IFN-gamma, GM-CSF (granulocyte/macrophage colony stimulating factor), PF-4 (Platelet factor 4), and RANTES (a member of the chemokine family). The examples describe measuring the activity of TNF-α in diabetic foot ulcer fluid from two patients. The data showed elevated TNF-α in the patient who subsequently developed infection. No measurement of bacterial bioburden in the wounds was carried out.

US-A-2007053962 describes methods of diagnosis or prognosis of a mammalian wound infection comprising the step of measuring the level of at least one cell surface receptor in a sample of wound fluid. The preferred cell surface receptors are Intercellular adhesion molecule-1 (ICAM 1) and Tumor Necrosis Factor Receptor-2 (TNF-R2). The examples present data for venous leg ulcers showing that the levels of both ICAM 1 and TNF-R2 increase with bacterial bioburden by approximately an order of magnitude over the range of bioburden studied.

GB-A-2430031 describes methods for the diagnosis or prognosis of wound infection comprises measuring the level of interleukin-4 (IL-4) in a sample of wound fluid. An elevated level is indicative of wound infection. The example shows positive correlation of measured IL-4 activity to bacterial bioburden in venous ulcer fluid.

US-A-2007053961 describes methods of diagnosis or prognosis of a mammalian wound infection, comprising the step of measuring the level of at least on angiogenic factor in a sample of wound fluid. Suitably, the angiogenic growth factors are selected from the group consisting of acidic fibroblast growth factor (FGF-1), granulocyte colony stimulating factor (G-CSF), basic fibroblast growth factor (FGF-2), hepatocyte growth factor scatter factor (HGF/SF), vascular endothelial growth factor, vascular permeability factor (VEGF/VPF), pleiotrophin, transforming growth factor-[alpha] (TGFα), proliferin, transforming growth factor-[beta] (TGFβ), follistatin, tumor necrosis factor-[alpha] (TNFα), placental growth factor (P1GF), angiogenin, midkine, interleukin-3 (IL-3), platelet-derived growth factor-BB (PDGF-BB), interleukin-8 (IL-8), fractalkine and platelet-derived endothelial cell growth factor (PD-ECGF). The examples show an increase in VEGF level with increasing bacterial bioburden in venous leg ulcer fluids.

DISCLOSURE OF THE INVENTION

The present inventors have made the surprising discovery that the level of certain cytokines in certain wound samples, such as diabetic ulcer samples, inversely correlates with the microbial bioburden in the wound, and thus that a low level of a relevant cytokine in a wound is indicative of wound infection. The data therefore suggest that low cytokine levels can be important markers for the diagnosis and prognosis of wound infection.

Without wishing to be bound by any hypothesis, the inventors conclude that the level of these cytokines in wound fluid is determined by the balance between increased production of these cytokines by the inflammatory response and increased destruction of these cytokines by elevated proteinase levels that are present in chronic wounds. It is hypothesised that the underlying pathology of diabetic foot ulcers, may be a contributing factor, with these ulcers unable to mount an efficient immune response to microbial contamination. For example, diabetic foot ulcers seem to be characterised by an inability to attract sufficient numbers of inflammatory cells into the wound. The observed decreases in cytokine levels also coincided with significantly increased elastase-like activity, in the diabetic foot ulcer wound fluids.

The present inventors have also found that the correlation between clinical signs of infection and actual measured bioburden in the wounds that were studied is poor, with the clinical diagnosis giving a number of false positives and false negatives for wound infection as measured by bacterial bioburden. This may account for the positive correlation between TNFα level and subsequent clinical determination of wound infection reported in WO-A-2004086043.

The present invention therefore provides new diagnostic and prognostic assays to monitor patients for wound infection. Standard diagnostic technology (e.g. immunodetection) can be used to detect the cytokines. Antibodies which detect cytokines may be employed, and are available commercially. The assays of the invention may be laboratory-based, or they may be carried out at the point of care.

In one aspect, the present invention provides a method of determining the microbial bioburden in a wound in a test subject, the method comprising the step of measuring the level of a cytokine in a wound sample, wherein a measured cytokine level lower than a reference level indicates a significant microbial bioburden in the wound (or a measured cytokine level higher than a reference level indicates an insignificant microbial bioburden in the wound).

A "significant microbial bioburden" is a microbial bioburden which warrants prophylactic or therapeutic intervention with antimicrobial agents (i.e. it is indicative of clinical infection). Where the wound sample is a wound fluid sample, a significant microbial bioburden may be a microbial bioburden of $>1\times10^5$, $>1\times10^6$ or $>1\times10^7$ CFU/ml. Where the wound sample is a wound tissue sample, a significant microbial bioburden may be a microbial bioburden of $>1\times10^4$, $>1\times10^5$ or $>1\times10^6$ CFU/g.

An "insignificant microbial bioburden" is a microbial bioburden which does not warrant prophylactic or therapeutic intervention with antimicrobial agents (i.e. it is not indicative of clinical infection). Where the wound sample is a wound fluid sample, an insignificant microbial bioburden may be a microbial bioburden of $<1\times10^5$, $<1\times10^6$ or $<1\times10^7$ CFU/ml. Where the wound sample is a wound tissue sample, an insignificant microbial bioburden may be a microbial bioburden of $<1\times10^4$, $<1\times10^5$ or $<1\times10^6$ CFU/g.

The microbial bioburden of a wound is the number of microbes with which the wound in contaminated. The microbial bioburden of a wound is commonly expressed as colony forming units per gram (CFU/g) of tissue for wound tissue samples, and as colony forming units per liter (CFU/ml) of fluid for wound fluid samples.

Fragments or breakdown products of the relevant cytokines may be measured in the methods of the invention. Such fragments and breakdown products include low molecular weight peptides that are derived from the cytokine as a consequence of protease activity. Accordingly, references to measuring the level of a cytokine herein encompass measuring the level of fragments or breakdown products of the cytokine.

Moieties which interact with the relevant cytokines may also be measured in the methods of the invention. Suitably, the moiety interacts specifically with the cytokine, e.g. the moiety might be a cytokine receptor which binds specifically to the cytokine.

The measurement of the cytokine level may be qualitative. Thus, in some methods the presence or absence of the cytokine is determined. Alternatively, a quantitative or semi-quantitative test for the cytokine may be performed. Thus, in some embodiments the concentration of a cytokine is measured. Accordingly, references herein to measuring the level of a cytokine include both detecting the presence or absence of a cytokine and measuring the concentration of a cytokine.

A "lower" (or "higher") level of a cytokine is a level where the measured level is significantly lower (or significantly higher) than the reference (control) level. By "significantly lower" (or "significantly higher") is meant that there is a statistically significant difference between the measured level and the reference level. Thus, the level of a cytokine is significantly lower (or higher) than the reference level if the measured level is lower (or higher) than the reference level by an amount greater than the standard error of the assay employed to measure the level of the cytokine, and suitably at least twice, and more suitably three, four, five or ten times that amount. Alternatively, the level of the cytokine can be considered significantly lower (or higher) than the reference (control) level if the measured level is at least about 1.5, 2, 3, 4 or 5 times lower (or higher) than the reference level.

The specific reference (control) level chosen will depend on the desired result of the analysis. An appropriate reference level can be selected by the skilled person.

For a qualitative analysis, the specific reference level selected is not crucial, although it should be selected so that the method provides a useful diagnostic or prognostic indication when the measured level of the cytokine is lower (or higher) than the reference level.

For a quantitative analysis, the reference level may be characteristic of a known microbial bioburden. In such embodiments, a measured cytokine level lower (or higher) than the reference level indicates that the microbial bioburden in the wound is higher (or lower) than the known microbial bioburden. For example, where the wound sample is a wound fluid sample, the reference level may be characteristic of a microbial bioburden of $1\times10^3$, $1\times10^4$, $1\times10^5$, $1\times10^6$, $1\times10^7$, $1\times10^8$ or $1\times10^9$ CFU/ml. Where the wound sample is a wound fluid sample, the reference level is suitably characteristic of a microbial bioburden of $1\times10^5$, $1\times10^6$ or $1\times10^7$ CFU/ml. Where the wound sample is a wound tissue sample, the reference level may be characteristic of a microbial bioburden of $1\times10^2$, $1\times10^3$, $1\times10^4$, $1\times10^5$, $1\times10^6$, $1\times10^7$ or $1\times10^8$ CFU/g. Where the wound sample is a wound tissue sample, the reference level is suitably characteristic of a microbial bioburden of $1\times10^4$, $1\times10^5$ or $1\times10^6$ CFU/g.

Thus, in some embodiments of this aspect of the invention, the method comprises comparing the measured level of the cytokine in the wound sample to a reference level characteristic of a known microbial bioburden, wherein a measured cytokine level lower than the reference level indicates a higher microbial bioburden in the wound (or a measured cytokine level higher than the reference level indicates a lower microbial bioburden in the wound).

Infected wounds contain a greater microbial bioburden than non-infected wounds. Thus, the methods of the invention can be used to identify infected and non-infected wounds. It has been found that levels of certain cytokines are significantly decreased in infected wounds relative to non-infected wounds, so a difference in cytokine levels between different wound samples is significant. Levels of the relevant cytokines in a wound sample are therefore useful as a diagnostic or prognostic of wound infection.

Accordingly, in a further aspect the present invention provides a method of identifying an infected wound in a test subject, the method comprising the step of measuring the level of a cytokine in a wound sample, wherein a measured cytokine level lower than a reference level indicates the presence of infection in the wound (or a measured cytokine level higher than a reference level indicates the absence presence of infection in the wound).

In some embodiments of this aspect of the invention, the method comprises comparing the measured level of the cytokine in the wound sample to a reference level characteristic of a non-infected wound, and wherein a measured cytokine level lower than the reference level indicates the presence of infection in the wound (or a measured cytokine level higher than the reference level indicates the absence of infection in the wound). In embodiments where the wound sample is a wound fluid sample, the reference level characteristic of a non-infected wound is suitably characteristic of a microbial bioburden of $1\times10^5$, $1\times10^6$ or $1\times10^7$ CFU/ml. In embodiments where the wound sample is a wound tissue sample, the reference level characteristic of a non-infected wound is suitably characteristic of a microbial bioburden of $1\times10^4$, $1\times10^5$ or $1\times10^6$ CFU/g.

In further embodiments, the method comprises obtaining wound samples from a test subject at intervals of from about 1 hour to about 24 hours and measuring the level of a cytokine in the samples obtained. Such methods allow changes in the level of the cytokine over time to be observed. A decrease in the cytokine level over time would be strongly indicative of developing infection, whereas an increase in the cytokine level over time would be strongly indicative of declining infection.

In some embodiments, the method further comprises measuring the total protein content of the wound sample and normalising the measured level of the cytokine to the total protein content. This allows variation in the rate of production and concentration of the wound sample to be corrected. For example, total protein content can be determined using the Bradford protein assay (Bradford M M, Anal. Biochem. 1976, 72:248-254).

In some embodiments, the methods of the invention involve identification of specific areas of infection within a wound. Unnecessary treatment of healthy granulating tissue can be avoided if the infected areas within a wound that require prophylactic or curative action are identified. Thus, a method of determining the microbial bioburden in a wound, or of identifying an infected wound, may comprise measuring the level of a cytokine in a plurality of different areas of a wound (e.g. 2 or more, 3 or more, 4 or more or 5 or more different areas of a wound). Devices suitable for such wound mapping methods are described elsewhere herein.

In many cases, a physician may not actually require an accurate quantitative measurement of the cytokine level, and may instead only require a qualitative measurement to enable a decision to be taken on the need for prophylactic or curative action. In these cases, visual assessment of a biosensor device may be sufficient to allow a decision to be taken on the need for prophylactic or curative action, or to allow identification of specific areas of infection within a wound.

In a further aspect, the present invention provides a method for the treatment of a mammalian wound, comprising the steps of measuring the level of a cytokine in a wound sample, and applying an antimicrobial wound dressing to the wound if the measured level of the cytokine is lower than a reference level.

The wound dressing materials useful in the methods of the present invention may for example be provided in the form of beads, flakes, powder, and suitably in the form of a film, a fibrous pad, a web, a woven or non-woven fabric, a freeze-dried sponge, a foam or combinations thereof. In certain embodiments, the wound dressing material is selected from the group consisting of woven fabrics, knitted fabrics, and nonwoven fabrics, all of which may be made by conventional methods. In other embodiments, the material may comprise (or consist essentially of) a freeze-dried sponge or a solvent-dried sponge.

The wound dressing material may be in the form of a solid, or a semi-solid ointment or gel. Suitably, the wound dressing material comprises only up to 20% by weight, suitably less than 10% by weight of water. The relatively low water content improves the stability of the material and makes it possible to sterilize by heat or irradiation without loss of activity. The material may also contain 0-40% by weight, suitably 0-25% by weight of a plasticiser, suitably a polyhydric alcohol such as glycerol. All of the above percentages are on a dry weight basis.

A wound dressing is "antimicrobial" if it comprises a pharmaceutically effective amount of an antimicrobial agent. The antimicrobial agent may be selected from the group consisting of antiseptics and antibiotics and mixtures thereof. Suitable antibiotics include peptide antimicrobials (e.g. defensins, Magainin, synthetic derivatives of them) tetracycline, penicillins, terramycins, erythromycin, bacitracin, neomycin, polymycin B, mupirocin, clindamycin and mixtures thereof. Suitable antiseptics include silver sulfadiazine, chlorhexidine, povidone iodine, triclosan, other silver salts and colloidal silver, sucralfate, quaternary ammonium salts and mixtures thereof.

In a further aspect, the present invention provides a method for the treatment of a mammalian wound, comprising the steps of measuring the level of a cytokine in a wound sample, and applying a non-antimicrobial wound dressing to the wound if the measured level of the cytokine is higher than a reference level.

A wound dressing is "non-antimicrobial" if it does not comprise a pharmaceutically effective amount of an antimicrobial agent. The use of a non-antimicrobial wound dressing to treat a non-infected wound avoids unnecessary application of antimicrobial agents to the wound, which is undesirable because most antimicrobial agents are cytotoxic and interfere with wound healing, and also to avoid the development of resistant microorganisms.

A method of treatment as described herein may comprise obtaining wound samples from a test subject at intervals, for example at intervals of from 1 hour to 24 hours, and selecting an antimicrobial or non-antimicrobial wound dressing to treat the wound at each interval in response to the measured level of the cytokine. An antimicrobial or non-antimicrobial dressing may be selected in response to the level of the cytokine or in response to changes in the measured level of the cytokine. For example, an antimicrobial wound dressing may be applied to a wound if the cytokine level is decreasing over time, and the non-antimicrobial dressing applied if the cytokine level is increasing over time.

The methods of the invention may be performed on a wound sample that has been removed from the body (e.g. a tissue sample or a fluid sample) but can also be performed in situ. The decision as to which type of method is used will depend upon the type of wound being studied. Suitably, the method is an in vitro method performed on a wound sample that has been removed from a test subject.

In some embodiments, the method is performed on a wound fluid sample. A wound fluid sample may be extracted directly from the environment of the wound, or can be washed off the wound using a buffer (e.g. a saline buffer). Methods in which a wound fluid sample is washed off the wound will be preferable for cases where the wound is too small or too inaccessible to allow access of a diagnostic or prognostic device such as a dipstick. Such methods have the additional advantage that the wound exudate sample may be diluted. The resulting diluted fluid can then be assayed for the level of a cytokine in, e.g. a test tube or a microtitre plate.

As used herein, the term "wound fluid" is meant to refer to any wound exudate or other fluid that is secreted or discharged by cells in the environment of the wound, which is suitably substantially free of blood. The term "wound fluid" does not normally refer to blood or tissue plasma remote from the wound site. A "wound fluid sample" may be present at the surface of a wound, or may have been removed from a wound by aspiration, absorption or washing.

When the method is performed on a wound fluid sample, the level of the cytokine may be measured in a fully aqueous assay system, or one or more reaction components may be immobilized on a substrate (as described elsewhere herein). It will be clear that an aqueous assay system is more applicable to use in a laboratory environment, whereas use of a substrate having one or more of the necessary reaction components immobilised on it will be more suitable for use in a hospital or domestic environment.

The methods of the present invention may be performed on any type of wound. The wound may be an acute wound, such as an acute traumatic laceration, perhaps resulting from an intentional operative incision. The wound may be a chronic wound, such as a venous ulcer, a pressure sore, a decubitis ulcer, a diabetic ulcer or a chronic ulcer of unknown aetiology. In preferred embodiments, the wound is a diabetic ulcer, in particular a diabetic foot ulcer.

In some embodiments, the wound is an external (open) wound, wherein the skin has been broken and the underlying tissue is exposed. Alternatively, the wound may be an internal (closed) wound, wherein the skin has not been broken but trauma to the underlying tissue has occurred. In the case of surface-exposed wounds, a biosensor device may be applied directly to the surface of the wound. The device can then be removed from the wound and the level of the cytokine(s) measured by an appropriate method.

The methods and devices of the present invention may be used in the diagnosis, prognosis and treatment of wound infection in both human and non-human mammals. The test subject is suitably a human, more suitably a diabetic human.

Various types of method may be used to measure the level of the cytokine(s). Suitable methods include those utilising chemical or enzyme-linked reactions (e.g. PCR), or immunological methods (e.g. ELISA, western blots), spectrophotometric, colorimetric, fluorimetric, or radioactive detection based techniques. The use of an immunological method (immunoassay) is preferred.

The methods of the invention require the level of a relevant cytokine to be measured. The inventors have identified a number of relevant cytokines (see the Examples herein). The skilled person will easily be able to identify further relevant cytokines which act as prognostic and diagnostic markers of wound infection in addition to those disclosed herein.

Cytokines are usually split into two groups—those that promote an inflammatory response (proinflammatory cytokines) and those that help suppress this response (anti-inflammatory cytokines). Some examples of pro-inflammatory cytokines are TNF-$\alpha$, IL-1$\beta$, IL-6, IL-8, RANTES and MIP-IB. Some examples of members of anti-inflammatory cytokines are IRAP, IL-4, IL-10, IL-11, IL-13, IP-10, MCP1 and TGF-$\beta$. The anti-inflammatory cytokines appear to be especially suitable for the practice of this invention.

Suitably, the cytokine is selected from the group consisting of interleukin-2 (IL-2), interleukin-4 (IL-4), interleukin-5 (IL-5), interleukin-10 (IL-10), interleukin-12 p40 (IL-12 p40), interleukin-12 p70 (IL-12 p70), interleukin-13 (IL-13), interferon-inducible protein 10 (IP-10), interferon gamma (IFN-$\gamma$), transforming growth factor-$\beta$1 (TGF-$\beta$1) and tumour necrosis factor-$\alpha$ (TNF-$\alpha$). For example, the cytokine may be selected from the group consisting of IL-2, IL-5, IL-10, IL-12 p40, IL-12 p70, IFN-$\gamma$ and TGF$\beta$1. In certain embodiments, the cytokine may be selected from the group consisting of IL-2, IL-5, IL-12 p40, and IL-12 p70.

IL-2 stimulates the growth, differentiation and survival of antigen-selected cytotoxic T cells, facilitates production of immunoglobulins by B cells, and induces the differentiation and proliferation of natural killer cells.

IL-4 promotes Th2 lymphocyte development; inhibits LPS-induced proinflammatory cytokine synthesis; stimulates activation, proliferation and differentiation of B cells, is a growth factor for T cells and mast cells, and has effects on granulocytes, mega-karyocyte and erythrocyte precursors and macrophages. IL-4 is produced by activated T cells (Th2), mast cells, B cells and stromal cells.

IL-5 stimulates B cell growth and increases immunoglobulin secretion. IL-5 is also a key mediator in eosinophil activation. IL-5 is produced by produced by T cells (Th2) and mast cells.

IL-10 inhibits cytokine production by monocytes/macrophages and neutrophils, and inhibits the Th1-type lymphocyte response. IL-10 is produced by monocytes/macrophages, T cells (Th2) and B cells.

IL-12 p70 is a 70 kD heterodimer composed of IL-12 p35 (35 kD) and IL-12 p40 (40 kD) monomers. IL-12 p70 stimulates the production of interferon-gamma (IFN-$\gamma$) and tumor necrosis factor alpha (TNF-$\alpha$) from T and natural killer (NK) cells, and reduces IL-4 mediated suppression of IFN-$\gamma$. IL-12 also has anti-angiogenic activity. IL-12 p70 is produced by monocytes, macrophages, and dendritic cells.

IL-13 shares homology with IL-4 and shares IL-4 receptor attenuation of monocyte/macrophage function. IL-13 is produced by T cells (Th2).

IP-10 is an angiostatic chemokine which blocks angiogenesis through interaction with CXCR3-B. IP-10 is produced by endothelial, monocyte, fibroblast and keratinocyte cells.

IFN-γ is an inhibitor of viral replication and a regulator of immunological function.

TGF-β1 suppresses cell proliferation, inhibits monocyte/macrophage MHC class II expression and proinflammatory cytokine synthesis and enhances extracellular matrix deposition. TGF-β1 is constitutively expressed in many cell lines.

TNF-α is a pro-inflammatory cytokine with a variety of effects. TNF-α is mainly produced by macrophages, but also by a broad variety of other cell types including lymphoid cells, mast cells, endothelial cells, fibroblasts and neuronal tissue.

Surprisingly, the inventors have found that levels of certain pro-inflammatory cytokines (which are generally thought to be induced upon injury and are elevated and prolonged in chronic or delayed would healing) are actually decreased in some infected wounds relative to non-infected wounds.

In some embodiments, the cytokine is an interleukin. The interleukins have similar structures, although they have varied functions. For example, the cytokine may be an interleukin selected from the group consisting of IL-2, IL-4, IL-5, IL-10, IL-12 p40, IL-12 p70 and IL-13.

In some embodiments, the cytokine is an interleukin associated with T cell development or regulation of the TH1/TH2 cell response. For example, the cytokine may be an interleukin selected from the group consisting of IL-2, IL-4, IL-12 p40, IL-12 p70 and IL-13.

In other embodiments, the cytokine is IP-10, IFN-γ, TGFβ1 or TNF-α.

As noted elsewhere herein, moieties which interact with the relevant cytokines may also be measured in the methods of the invention (e.g. cytokine receptors). For example, in some embodiments, the level of tumor necrosis factor receptor 2 (TNFr2), which is the TNF-α receptor, is measured.

TNFr2 mediates similar actions to the pro-inflammatory cytokine TNF-α, such as T cell proliferation and cytokine production as well as other actions, such as the migration of Langerhans cells to lymph nodes. In normal skin, TNFr2 is not found in the epidermis, and is only associated with eccrine sweat ducts and dermal dendritic cells.

In further embodiments, levels of both TNF-α and TNFr2 may be measured.

IL-2, IL-5, IL-12 p40, IL-12 p70, IFN-γ, and TGF-β1 are suitably diagnostic and prognostic markers for use in the present invention, because were found to correlate significantly with microbial bioburden at both levels of microbial bioburden tested (see Example 2 herein). Accordingly, the cytokine is suitably a cytokine selected from the group consisting of IL-2, IL-5, IL-12 p40, IL-12 p70, IFN-γ, and TGF-β1. In certain embodiments, the cytokine may be selected from the group consisting of IL-2, IL-5, IL-12 p40, and IL-12 p70.

In some embodiments, the methods of the invention will comprise measuring the level of two or more cytokines in a wound sample.

In some embodiments, the methods of the invention will comprise measuring the level of three or more (four or more, five or more, six or more, etc.) cytokines in a wound sample.

The present invention also provides devices for use in the methods of the invention. The devices of the present invention comprise a selective binding partner, suitably a specific binding partner, for a cytokine.

A binding partner is "specific" if it has substantially greater affinity for the cytokine of interest than for other related molecules, e.g. other cytokines. By "substantially greater affinity" is meant that there is a measurable difference in the affinity of the binding partner for the cytokine of interest and for other related molecules, e.g. other cytokines. Suitably, the affinity of the binding partner for the cytokine of interest is at least 1.5-fold, at least 2-fold, at least 5-fold at least 10-fold, at least 100-fold, at least $10^3$-fold, at least $10^4$-fold, at least $10^5$-fold, at least $10^6$-fold or greater than its affinity for other related molecules, e.g. other cytokines.

The binding partner may be an immunological binding partner for the relevant cytokine(s). Suitable immunological binding partners will be known to the skilled person, and include antibodies, such as polyclonal and monoclonal antibodies. Suitable antibodies are readily available, e.g. from R&D Systems, Oxfordshire, UK (see the examples herein).

An immunological binding partner for use in the present invention may be specific for the relevant cytokine, as defined above.

If polyclonal antibodies are desired, a selected mammal, such as a mouse, rabbit, goat or horse, may be immunised with a cytokine. The cytokine used to immunise the animal can be obtained by any suitable technique, for example, it can be purified from a wound sample, it can be produced using recombinant DNA technology, or it can be synthesized chemically. If desired, the cytokine can be conjugated to a carrier protein. Commonly used carriers to which the cytokine may be chemically coupled include bovine serum albumin, thyroglobulin and keyhole limpet haemocyanin. The optionally coupled cytokine is then used to immunise the animal. Serum from the immunised animal is collected and treated according to known procedures, for example by immunoaffinity chromatography.

In some embodiments of the methods of the invention, fragments or breakdown products of the cytokine are measured. Fragments or breakdown products of the cytokine may be recognised by polyclonal antibodies that have been raised to the cytokine.

Monoclonal antibodies to the cytokine can be readily produced by one skilled in the art. The general methodology for making monoclonal antibodies using hybridoma technology is well known. Panels of monoclonal antibodies produced against the cytokine can be screened for various properties, e.g. for isotype, epitope, affinity. Alternatively, genes encoding monoclonal antibodies of interest may be isolated from hybridomas, for instance by PCR techniques known in the art, and cloned and expressed in appropriate vectors.

Chimeric antibodies, in which non-human variable regions are joined or fused to human constant regions may also be of use. Humanised antibodies may also be used. The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is, an antibody having two different antigen binding domains, each domain being directed against a different epitope.

Phage display technology may be utilised to select genes which encode antibodies with binding activities towards the cytokine either from repertoires of PCR amplified V-genes of lymphocytes from humans screened for possessing the relevant antibodies, or from naive libraries. The affinity of these antibodies can also be improved by chain shuffling.

In those embodiments of the invention where antibodies are used as the selective binding partner for the cytokine, the method can be an immunoassay, a radioimmunoassays (RIA) or an enzyme-linked immunosorbent assay (ELISA). The antibodies can be labelled with an analytically-detectable reagent such as a radioisotope, a fluorescent molecule or an enzyme.

As used herein, the term "antibody" refers to intact antibody molecules as well as to fragments thereof, such as Fab, F(ab')2 and Fv, which are capable of binding to the cytokine.

Alternatively, the selective binding partner may be derived from an endogenous moiety that interacts with the relevant cytokine(s), such as an endogenous cytokine receptor. In such embodiments, the endogenous moiety may be a specific binding partner for the relevant cytokine(s). The binding partner may comprise breakdown products or fragments of the host moiety, e.g. in the form of fusion proteins. Such binding partners may be specific for the relevant cytokine, as defined above.

In the devices for use in the present invention, the selective binding partner may be immobilized on a substrate. Various different types of substrate are suitable for use in the invention and are known to the skilled person. For example, the biosensor device may comprise or consist essentially of a swab, a wound dressing or a dipstick. Dipstick type devices are advantageous because they can be used in the community and/or by the patient allowing easier and earlier diagnosis or prognosis.

Methods for the incorporation of the components of an assay reaction onto a substrate are routine in the art, e.g. Fägerstam and Karlsson (1994) *Immunochemistry*, 949-970.

Immobilisation of reaction components, in particular of a selective binding partner for a cytokine, onto a solid or gel substrate offers the opportunity of performing a more quantitative measurement. For example, in the case of a reaction linked to the generation of a colour the device may be transferred to a spectrometer for quantitative measurement. Suitable methods of analysis will be apparent to those of skill in the art.

Immobilisation of the reaction components on a small biosensor device (e.g. a dipstick) will have the advantage that less of the reaction components (such as antibody, enzyme and substrate) are required. Such devices will thus be less expensive to manufacture than devices comprising larger amounts of the reaction components (e.g. a wound dressing that allows the mapping of infected areas within a large wound).

In some embodiments, the methods of the invention may involve identification of specific areas of infection within a wound. Unnecessary treatment of healthy granulating tissue can be avoided if the infected areas within a wound that require prophylactic or curative action are identified. Thus, a biosensor device (e.g. wound dressing) that allows mapping of the infected areas of a wound (e.g. a wound mapping sheet) will be preferable in certain instances. Diagnostic wound mapping sheets adaptable for use in the present invention are described in GB-A-2323166.

The device may further comprise a reference assay element for determining the total protein content of a wound sample, so that the measured level of the cytokine can be normalised to the total protein level in order to increase accuracy.

The detectable signal produced by a device according to the present invention is observable or measurable by a physical, chemical, or biological means known to those of skill in the art. A detectable signal may be a change in emission or absorbance of electromagnetic waves at a certain wavelength, hybridization or enzymatic reaction. In preferred embodiments, detectable signals are changes in colour when viewed under white light, or fluorescence when viewed under UV light. In certain embodiments, the device may comprise an electronic sensor, for example to detect color change or fluorescence and to provide a quantitative output thereof. The device may include an electronic sensor that can provide a quantitative output in digital form.

In use, a wound sample is applied to the device. Accordingly, the devices of the invention during use further comprise a wound sample disposed on the device.

The size and shape of the device is not critical and may vary. In some embodiments, a device according to the present invention may comprise a housing containing one or more reagents, an inlet provided therein for introduction of a wound fluid sample, and at least one flow path for sample analysis. Devices of this type adaptable for use in accordance with the present invention are described in patent publications GB-A-2415039, GB-A-2426335, GB-A-2430029, GB-A-2430030 and GB-A-2430031.

In certain embodiments of the present invention, the device may further comprise a control moiety which can interact with a component of the wound sample to improve the accuracy of the device. The control moiety may be adapted to reduce false positive or false negative results. Devices of this type adaptable for use in accordance with the present invention are described in patent publications GB-A-2415039, GB-A-2426335, GB-A-2430029, GB-A-2430030 and GB-A-2430031.

The devices according to the present invention may be adapted to detect more than one cytokine and/or one or more other analyte(s), as described in GB-A-2415039, GB-A-2426335, GB-A-2430029, GB-A-2430030 and GB-A-2430031.

The devices according to the present invention may be incorporated into a microbial sensing device of the kind described in GB-A-2422664.

An absorbent element may be included in the devices of the present invention, as described in GB-A-2415039, GB-A-2426335, GB-A-2430029, GB-A-2430030 and GB-A-2430031.

The device may further comprise at least one filtration element to remove impurities from the sample before the sample undergoes analysis, as described in GB-A-2415039, GB-A-2426335, GB-A-2430029, GB-A-2430030 and GB-A-2430031. For example, in order to address false negative results, the control moiety may comprise a reference assay element for determining the total protease content or the total protein content of the sample, i.e. for establishing that the total protease content or the total protein content of the sample is higher than a predetermined minimum. It is possible to indicate the presence of protein by the use of tetrabromophenol blue, which changes from colourless to blue depending on the concentration of protein present. It is also possible to detect glucose (using glucose oxidase), blood (using diisopropyl-benzene dihydro peroxide and tetramethylbenzidine), leukocytes (using ester and diazonium salt). These may all be useful analytes for detection by the control moiety for the reduction of false negatives.

The devices of the invention may comprise more than one different selective binding partner. For example, the devices of the invention may comprise N different selective binding partners, for N different cytokines, wherein N is 2 or more, 3 or more, 4 or more, 5 or more, 6 or more, etc.

The present invention also provides kits for use in the methods of the invention. In particular, the present invention provides a kit comprising a device of the invention and one or more components selected from the group consisting of (a) a would sampler for removing a wound sample from a test subject; (b) a chart for interpreting the output of the device; (c) a wash liquid for a wound sample; (d) a pre-treatment solution containing a reagent for pre-treatment of the wound sample; and (e) a wound dressing for application to a wound. The various components of the kit may be packaged together in a single package. For example, the kit may comprise two or more, three or more, four or more or all five of (a) a would sampler for removing a wound sample from a test subject; (b) a chart for interpreting the output of the device; (c) a wash liquid for a wound sample; (d) a pre-treatment solution containing a reagent for pre-treatment of the wound sample; and (e) a wound dressing for application to a wound in a single package.

The sampling device may comprise a swab or a biopsy punch, for example a shaft having a swab or biopsy punch attached thereto.

The swab may be any absorbent swab, for example a nonwoven fibrous swab. Typically the diameter of the swab is about 2 mm to about 5 mm, for example about 3 mm. In certain embodiments, the swab may be formed from a medically acceptable open-celled foam, for example a polyurethane foam, since such foams have high absorbency and can readily be squeezed to expel absorbed fluids.

The biopsy punch will typically be a stainless steel cylindrical punch of diameter about 1 mm to about 10 mm, for example about 3 mm to about 8 mm, suitably about 6 mm.

The wound sampler may be adapted for use in conjunction with the diagnostic device. For example, the device and the wound sampler may comprise complementary fitting elements, such that the wound sampler can be secured to the device with the wound sampler received in a sample receiving port. Wound samplers of this type adaptable for use in the present invention are described in GB-A-2411230, GB-A-2411231, GB-A-2415039, GB-A-2426335, GB-A-2430029, GB-A-2430030 and GB-A-2430031.

In some embodiments, the wound sampler may comprise a hollow shaft, whereby a fluid can be passed down the shaft to expel the wound sample from the wound sampler into the diagnostic device. Suitable wound samplers are described in GB-A-2415039, GB-A-2426335, GB-A-2430029, GB-A-2430030 and GB-A-2430031.

The wound sampler may be sterilized, and may be packaged in a microorganism-impermeable container. The diagnostic devices according to the present invention may also be sterilized, although this is not essential, because the devices often do not come into contact with the patient being diagnosed.

The chart for interpreting the output of the device may be a colour chart, a graph or a table.

The kits of the invention may comprise antimicrobial and/or non-antimicrobial wound dressings as described elsewhere herein.

MODES FOR CARRYING OUT THE INVENTION

Materials and Methods

Patients ($\geq$18 years old) were included in the study on the basis they had a venous leg or diabetic foot ulcer for $\geq$30 days, of at least 1 cm$^2$ in area, with exudates flow. Subjects were excluded if the target wound demonstrates signs of infection (only applicable for the non-infected wound categories), the wound was dry and/or predominantly healed, exhibited exposed bone and positive osteomyelitis, or if the patient had a concurrent illness or condition that may interfere with wound healing, was a known alcohol or drug abuser, receiving dialysis, or had received corticosteroids, immuno-suppressive agents, radiation therapy or chemotherapy within the 30 days, prior to enrolment.

Ten (10) subjects with venous leg ulcers and ten (10) subjects with diabetic foot ulcers were enrolled into the clinically non-infected groups. These subjects exhibited no clinical signs of infection. These collected wound fluid samples generated baseline data for each biochemical marker believed to be important in the host response to infection and also used to determine intra-patient variability. Each subject contributed a single wound fluid collection. Ten (10) subjects with venous leg ulcers and five (5) subjects with diabetic foot ulcers were enrolled into the clinically infected groups. These patients exhibited clinical symptoms of infected chronic wounds, demonstrating a minimum of four of the following: evidence of cellulites, localised pain, swelling, erythema, increased local skin temperature, unhealthy granulation tissue, abnormal colour, pus and increased exudates. These clinical signs and symptoms were assigned by the principle Clinical Investigator of this study. The wound fluid samples were analysed for the same biochemical markers, as in the non-infected groups, and the data also used to determine intra-patient variability and to ascertain if any of these markers could be used in chronic wound infection diagnosis/prognosis.

The wounds of the enrolled subjects in both groups (clinically non-infected and infected) were swabbed for microbiological analysis. Analysis included the quantification and characterisation of aerobic and anaerobic bacteria, fungi and yeast using standardised microbial culture techniques. Swabs were taken of the wound and microorganisms cultured on fresh blood agar, MacConkey 3 agar, Sabouraud dextrose agar and Fastidious Anaerobic agar at 32 or 37° C., in the presence or absence of oxygen, allowing for the detection of total microflora, entero-bacteria, yeasts and anaerobes, respectively. Cultures were maintained for up to 14 days to allow for the detection of anaerobic organisms.

Swabs were transferred to the laboratory in transport medium, mixed and serially diluted, for example 1:10, in an appropriate broth. A defined volume of each dilution (including the original suspension), was taken, inoculated on the individual agar types, as described above, and incubated appropriately. The number of colony forming unit (CFU) per microbiological isolate, were counted on a selected agar plate that allowed for individual colonies to be counted, typically a plate containing 30-300 CFU. The number of CFU/ml was calculated, based upon the volume of inocula and dilution factor applied.

Microorganisms were identified by both macroscopic and microscopic examination of phenotypic properties including, colonial morphology, staining reactions, and other standard identification techniques, such as, but not limited to, catalase/oxidase reactions. Where appropriate, the use of commercial identification kits was employed.

After the wound swabs were obtained, the wounds were debrided, if necessary, cleansed with normal saline and dried. The area of each wound was then traced onto a wound measuring acetate and a photographic record of the wounds made.

For wound fluid collection, each venous leg ulcer and diabetic foot ulcer was dressed with RELEASE® and covered with a BIOCLUSIVE® film dressing. These dressings remained in situ up to 4 hrs (in the case of the venous leg ulcers) or as long as overnight (in the case of the diabetic foot ulcers). Upon wound dressing saturation, the BIOCLUSIVE® film was removed, and saturated RELEASE® dressing removed using sterile forceps and placed in a sterile vial on dry ice for storage at −80° C. Any non-saturated regions on the RELEASE® dressings were removed using sterile scissors. In order to elute the wound fluids, wound dressings were measured and immersed in 0.1 M Tris-HCl buffer, pH 7.4, containing 0.1% Triton X-100 (wound fluid elution buffer, 500 µl buffer/cm2 dressing) and eluted for 2 h, at 4° C., under constant agitation. Eluted wound fluid samples were aliquoted and stored at −80° C., until required.

Cytokine levels were measured by ELISA. ELISA kits and antibodies for individual cytokines were used according to manufacturer's instructions (R&D Systems, Oxfordshire, U.K.). Cytokine micro-array analysis was conducted on collected wound fluid samples according to Schleicher and Schuell (S&S) standard operating procedures, utilising 16-pad FAST slides, arrayed with all anti-cytokine specificities (monoclonal antibodies arrayed in triplicate) (see Table 1 below). Antibodies were arrayed using a piezo-electric Perkin-Elmer BioChip Arrayer (Perkin-Elmer, Buckinghamshire, UK). Slides were processed in a FastFrame (64 pads, with 96-well spacing).

Microarray antibodies were sourced as matched antibody pairs (from R&D Systems). Each antibody IgG fraction was purified by either protein A or G affinity chromatography. Each antibody is specific for the human version of the cytokine, exceptions are highlighted with * and this denotes that these antibodies also cross-react with some animal species.

TABLE 1

| Cytokine | Catalogue No. | Clone | Immunogen |
| --- | --- | --- | --- |
| IL-2 | MAB602 | 5355 | E. coli derived rh IL-2 |
| IL-4 | MAB604 | 3010 | E. coli derived rh IL-4 |
| IL-5* | MAB405 | TRFK5 | Partially purified rm IL-5 |
| IL-6 | MAB206 | HD27 | E. coli derived rh IL-6 |
| IL-8 | MAB208 | 6217 | E. coli derived rh CXCL8 |
| IL-10 | MAB217 | 23738 | Sf 21-derived rh IL-10 |
| IL-12 p40 | MAB609 | 31052 | Sf 21-derived rh IL-12/IL-23 p40 free monomer |
| IL-12 p70 | MAB611 | 24945 | Sf 21-derived rh IL-12 |
| IL-13 | MAB213 | 32116 | E. coli derived rh IL-13 |
| IP-10 | MAB266 | 33036 | E. coli derived rh IP-10 |
| IFNγ | MAB2852 | K3.53 | E. coli derived rh IFNγ |
| TGFβ1 | MAB240 | 9016 | CHO cell-derived TGFβ1 and latent TGFβ1 |
| TNF-α | MAB610 | 28401 | E. coli derived rh TNF-α |
| TNF r2 | MAB726 | 22210 | E. coli derived rh TNF r2 extracellular domain |
| IL-1β | MAB601 | 2805 | E. coli derived rh IL-1β |
| Angiogenin | MAB265 | 14017.7 | E. coli derived rh ANG |
| ICAM-1 | MAB720 | 14C11 | CHO cell-derived rh ICAM-1 extracellular domain |
| VEGF | MAB293 | 26503 | Sf 21-derived rh VEGF |

The total protein content of each extracted wound fluid sample was determined using the Bradford protein assay (Bradford M M, Anal. Biochem. 1976, 72:248-254). The protein binding solution comprises 1 ml Coomassie Brillant Blue stock solution (200 mg Coomassie Brillant Blue G250, Sigma Chemical Co., dissolved in 50 ml 90% ethanol) and 2 ml orthophosphoric acid (85% w/v) in a final volume of 20 ml with distilled water. This solution was filtered (Whatman #1 filter paper) and used immediately. The protein level in a sample of wound fluid was measured by mixing a 10 µl sample or standard with 190 µl of the protein binding solution in a microtitre well and incubating for 30 mins at ambient temperature prior to reading absorbance at 595 nm. The concentration of protein was estimated from a standard calibration of BSA (bovine serum albumin prepared in distilled water; Sigma Chemical Co.) ranging from 1.0 to 0.01 mg/ml.

REFERENCE EXAMPLE 1

Comparison of Venous Leg Ulcers and Diabetic Foot Ulcers

The inventors' previous work revealed that levels of certain cytokines in wound fluid correlate with the microbial bioburden in venous leg ulcers, and thus that increased cytokine levels can be used in the diagnosis and prognosis of venous leg ulcer infection (e.g. see the references listed above under Background to the Invention). In contrast, the inventors have now found that levels of certain cytokines in diabetic ulcer wound fluid inversely correlate with the microbial bioburden in diabetic ulcers, in particular diabetic foot ulcers, and thus that decreased cytokine levels can be used in the diagnosis and prognosis of diabetic ulcer infection, including diabetic foot ulcer infection.

Figure 1:
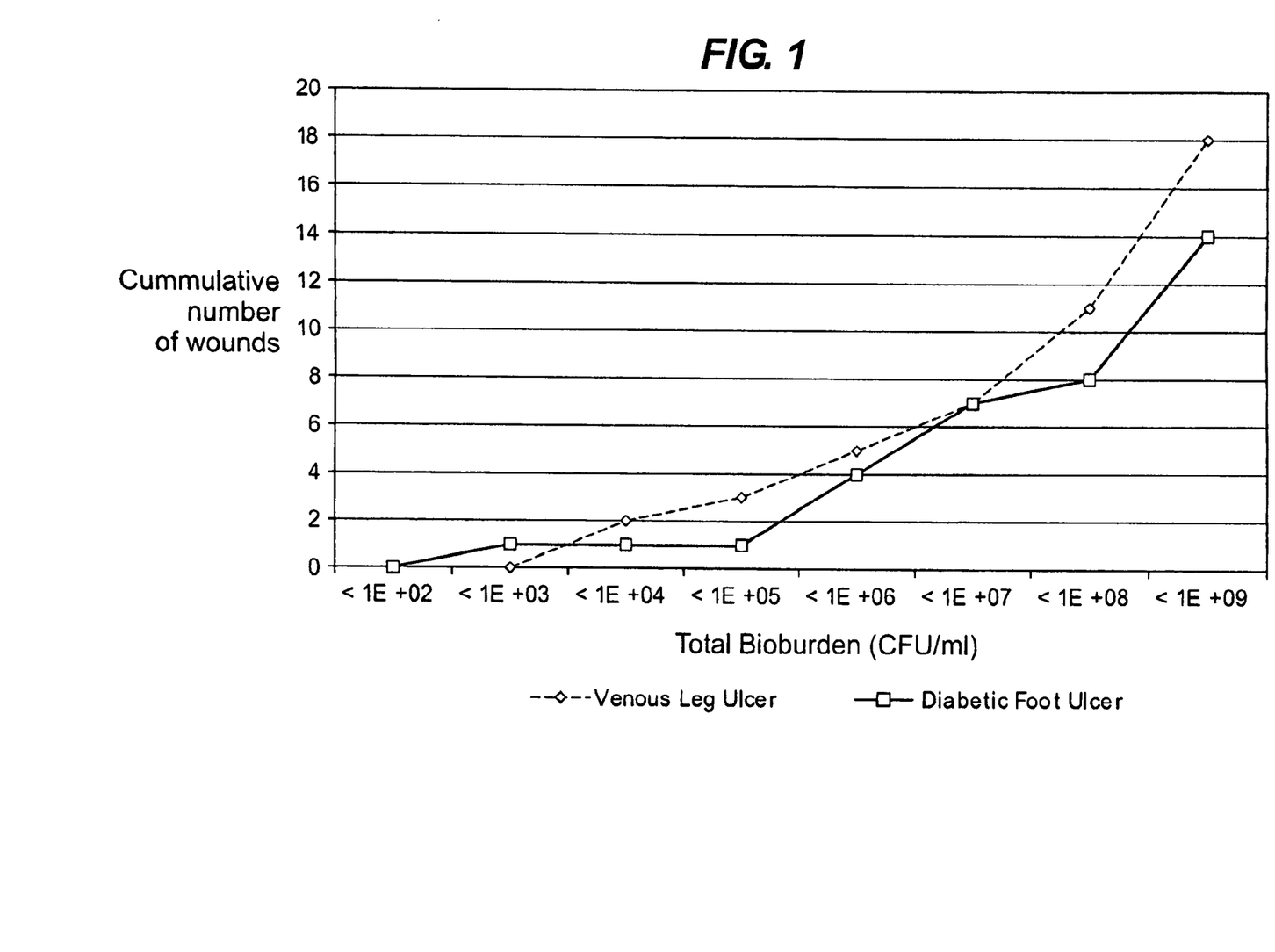
FIG. 1 shows a comparison of the microbial bioburden (measured in CFU/ml) in infected and non-infected venous leg ulcers and diabetic foot ulcers.

FIG. 1 shows a comparison of the microbial bioburden (measured in CFU/ml) in infected and non-infected venous leg ulcers and diabetic foot ulcers.

All of the wounds tested contained less than $1 \times 10^9$ CFU/ml (represented as <1E+09 on the graph). A high proportion of the wounds in both ulcer types contained a bioburden equal to or greater than $1 \times 10^5$ CFU/ml. Infection was defined microbiologically at a bioburden level equal or greater than $1 \times 10^6$ and $1 \times 10^7$ CFU/ml, for statistical analysis. It was found that the total bioburden of venous leg ulcers and diabetic foot ulcers is approximately the same.

Figure 2A:
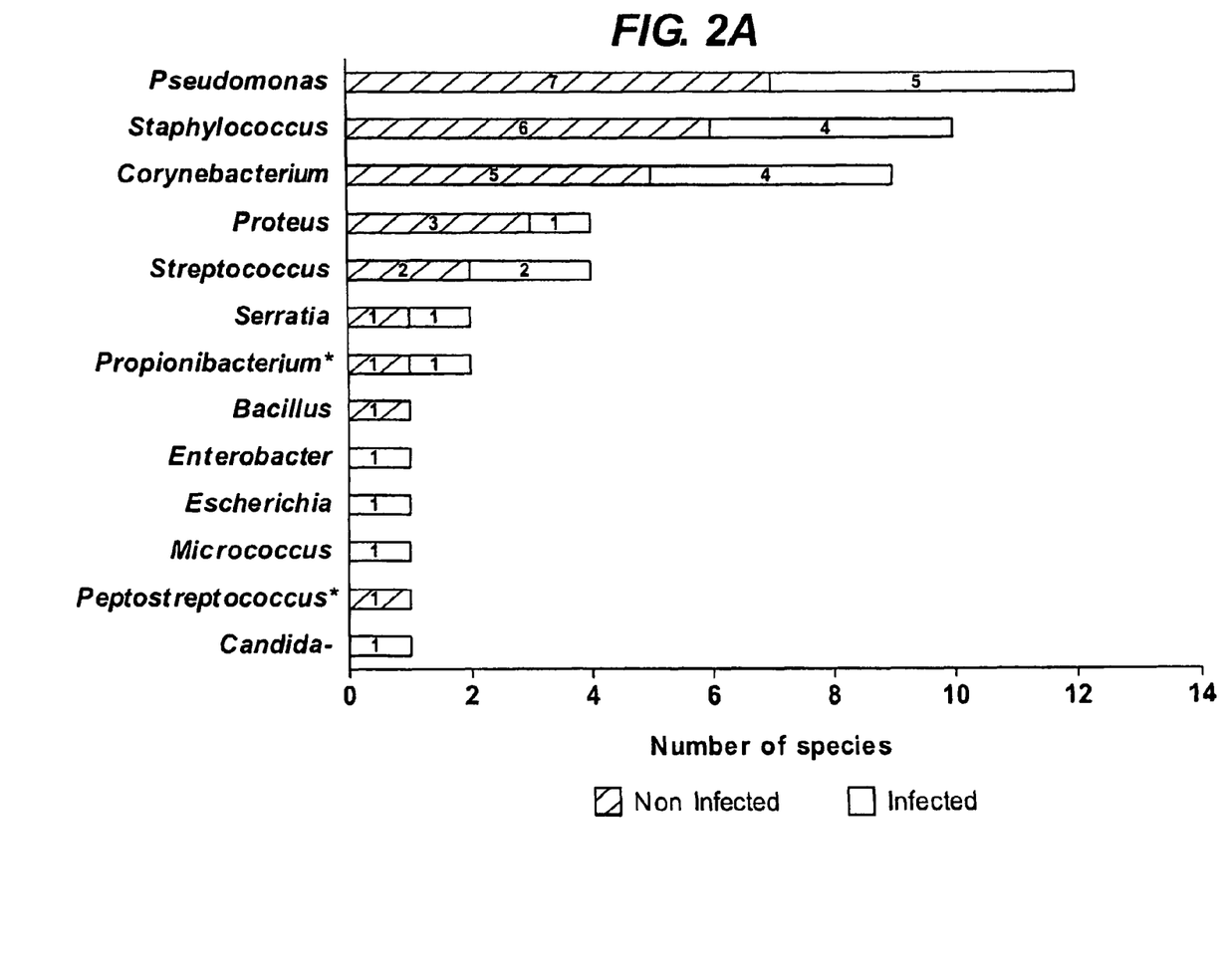
FIGS. 2A and 2B show the results of an analysis of the microbial flora in infected and non-infected venous leg ulcers and diabetic foot ulcers.
Figure 2B:
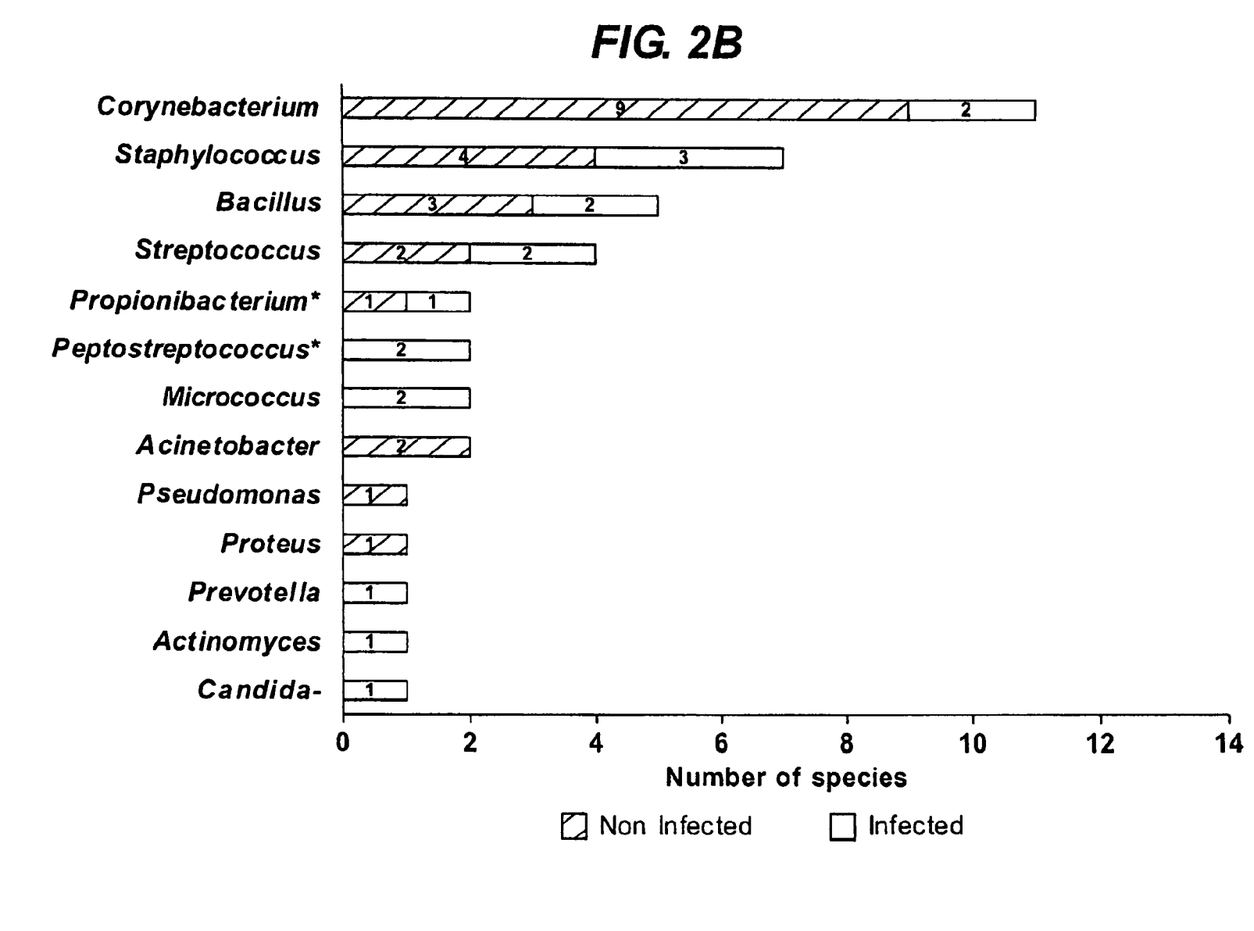

FIGS. 2A and 2B show the results of an analysis of the microbial flora in infected and non-infected venous leg ulcers and diabetic foot ulcers. It was found that the number and type of microbes (in particular, bacteria) differs between the two ulcer types. However, there was no significant difference in the number of genera identified in the non-infected and infected venous leg and diabetic foot ulcer wounds.

FIG. 2A illustrates the number of microbial species in clinically non-infected and infected venous leg ulcer wound fluid. The total bioburden ranged from $1 \times 10^3$ to $1 \times 10^8$ CFU/ml in the clinically non-infected and infected venous leg ulcer wounds. The most prominent species detected in venous leg ulcer wound fluid was Pseudomonas (12 of 18 wounds) and Staphlyococcus (10 of 18 wounds). Three wound fluids contained anaerobic bacteria (*), and one was contaminated with yeast (−).

FIG. 2B illustrates the number of microbial species in clinically non-infected and infected diabetic foot ulcer wound fluid. The total bioburden ranged from $1 \times 10^2$ to $1 \times 10^8$ CFU/ml in the clinically non-infected and infected diabetic foot ulcer wounds. In contrast, the most prominent species detected in diabetic foot ulcer wound fluid was the non-pathogenic Corynebacterium (11 of 14 wounds) and Staphlyococcus (7 of 14 wounds). Four wound fluids contained anaerobic bacteria (*).

The results of these experiments suggested that although the total bioburden in venous leg ulcers and diabetic foot ulcers is approximately the same, and there was no significant difference in the number of genera identified in wound fluid, there is a significant difference in the microbial flora between the two wound types.

Surprisingly, a comparison between clinical diagnosis and the measured total bioburden revealed that 9 out of the 18 wounds may have been misdiagnosed for venous leg ulcer wounds. Additionally, 6 out of the 14 wounds may have been misdiagnosed for diabetic foot ulcer wounds. This illustrates the importance of devising an objective method of determining total bacterial bioburden, rather than relying on clinical indicia for the diagnosis of wound infection.

EXAMPLE 2

Analysis of Diabetic Foot Ulcer Wound Fluid Samples

The inventors have investigated cytokine levels in diabetic foot ulcer wound fluids, and have found that levels of certain cytokines in wound fluid inversely correlate with the microbial bioburden in diabetic ulcers, in particular diabetic foot ulcers. The experimental results are summarised in the table below, which shows the amount of cytokine in microbiologically defined non-infected and infected diabetic foot ulcer wound fluid. The values are median values (in picogram/ml) for each cytokine in diabetic foot ulcer wound fluid that had a significant relationship with the microbial bioburden (ns=not significant).

It was found that within the diabetic foot ulcer population tested, some of the cytokines with significant differences at a bioburden level of $10^6$ CFU/ml did not all display significant differences at a level of $10^7$ CFU/ml. This change in significance was due to the type of statistical analysis employed, compounded by the limited number of samples in each population analysed. However, consistency was observed at both bioburden levels for IL-2, IL-5, IL-12 p40, IL-12 p70, IFN-γ, and TGF-β1. Accordingly, those cytokines are preferred for measurement in the methods of the invention.

TABLE 2

| Cytokine | Total Bioburden (CFU/ml) | | Significance | Total Bioburden (CFU/ml) | | Significance |
| --- | --- | --- | --- | --- | --- | --- |
| | >$10^6$ | <$10^6$ | p= | >$10^7$ | <$10^7$ | p= |
| IL-2 | 2.80 | 26.29 | 0.002 | 2.8 | 20.34 | 0.011 |
| IL-4 | 2.10 | 67.35 | 0.033 | 2.10 | 64.13 | 0.111* ns |
| IL-5 | 1.00 | 65.05 | 0.008 | 1.00 | 26.12 | 0.014 |
| IL-10 | 255.5 | 630.5 | 0.038 | 225.0 | 468.0 | 0.061* ns |
| IL-12 p40 | 2.50 | 600.00 | 0.027 | 2.00 | 318.28 | 0.033 |
| IL-12 p70 | 0.10 | 70.19 | 0.006 | 0.10 | 23.24 | 0.020 |
| IL-13 | 5.73 | 178.57 | 0.017 | 3.84 | 80.28 | 0.089* ns |
| IP-10 | 8.52 | 72.21 | 0.100* ns | 2.70 | 66.00 | 0.010 |
| IFN-γ | 0.20 | 21.54 | 0.010 | 0.20 | 4.64 | 0.034 |
| TGFβ1 | 1.20 | 84.54 | 0.006 | 1.20 | 65.93 | 0.020 |
| TNF-α | 14.57 | 102.13 | 0.076* ns | 2.22 | 83.62 | 0.040 |
| TNFr2 | 14290.3 | 109999.6 | 0.040 | 9530.5 | 46795.2 | 0.201* ns |
| n= | 7 | 7 | | 8 | 6 | |

REFERENCE EXAMPLE 3

Analysis of Venous Leg Ulcer Wound Fluid Samples

Table 3 shows the measured levels of cytokine in microbiologically defined non-infected and infected venous leg ulcer wound fluids. In contrast to the data for diabetic foot ulcer wound fluids in Example 2, median values for a number of cytokines in venous leg ulcer wound fluids exhibited a significant positive correlation with the levels of bacterial bioburden. Namely, the pro-inflammatory cytokines, IL-1β, IL-6 (FIG. 4.12a), the angiogenic cytokines, angiogenin and VEGF (FIG. 4.12b), cell surface receptors, ICAM and TNFr2, and TNF-α, and the T-cell differentiating cytokine, IL-4.

The most significant relationships discriminating venous leg ulcers wound fluids with bacterial bioburden level of $1 \times 10^6$ CFU/ml and at a level of $1 \times 10^7$ CFU/ml, were IL-1β (p=0.004), and IL-4 (p=0.001), respectively.

TABLE 3

| Cytokine | Total Bioburden (CFU/ml) $>10^6$ vrs $<10^6$ | | Significance (p values) | Total Bioburden (CFU/ml) $>10^7$ vrs $<10^7$ | | Significance (p values) |
|---|---|---|---|---|---|---|
| IL-1β | 1250.2 | 215.4 | 0.004 | 1309.0 | 348.1 | 0.011 |
| IL-4 | 75.4 | 26.2 | 0.006 | 83.7 | 40.6 | 0.001 |
| Angiogenin | 5282.0 | 561.6 | 0.025 | 6768.0 | 973.2 | 0.011 |
| IL-6 | 7328.5 | 203.6 | 0.006 | 7997.2 | 614.4 | 0.008 |
| ICAM-1 | 1604.2 | 396.9 | 0.009 | 1644.3 | 653.8 | 0.003 |
| TNF-α | 127.7 | 20.9 | 0.018 | 167.1 | 40.0 | 0.034 |
| TNFr2 | 54114.0 | 7718.0 | 0.006 | 58427.0 | 21880.0 | 0.015 |
| VEGF | 14385.0 | 4205.0 | 0.013 | 14385.0 | 7070 | 0.034 |
| n= | 13 | 5 | | 11 | 7 | |

The above examples have been described by way of example only. Many other examples falling within the scope of the accompanying claims will be apparent to the skilled reader.

The invention claimed is:

1. An in vitro method of determining the microbial bioburden in a diabetic ulcer in a test subject, the method comprising the step of measuring the level of a cytokine in a diabetic ulcer sample selected from the group consisting of a fluid sample and a tissue sample, wherein a measured cytokine level at least 1.5 times lower than a reference level indicates a significant microbial bioburden in the diabetic ulcer, wherein the cytokine is IL-2, and further wherein a significant microbial bioburden in a diabetic ulcer fluid sample is greater than $1 \times 10^5$ CFU/ml and a significant microbial bioburden in a diabetic ulcer tissue sample is greater than $1 \times 10^4$ CFU/ml.

2. A method according to claim 1, wherein the method comprises obtaining diabetic ulcer samples from a test subject at intervals of from about 1 hour to about 24 hours and measuring the level of a cytokine in the samples obtained.

3. A method according to claim 1, wherein the method further comprises measuring the total protein content of the diabetic ulcer sample and normalising the measured level of the cytokine to the total protein content.

4. A method according to claim 1, wherein the ulcer is a diabetic foot ulcer.

5. A method according to any claim 1, wherein the level of the cytokine is determined by an immunoassay.

6. A method according to claim 5, wherein the immunoassay is an enzyme-linked immunosorbant assay (ELISA).

7. A method according to claim 1, which comprises measuring the level of two or more cytokines in a diabetic ulcer sample, wherein at least one cytokine is IL-2.

8. A method according to claim 7, wherein the two or more cytokines are selected from the group consisting of IL-2, IL-5, IL-12 p40, IL-12 p70, IFN-γ, and TGF-β1, further wherein at least one cytokine is IL-2.

9. A method according to claim 8, which comprises measuring the level of three or more cytokines in a diabetic ulcer sample, wherein at least one cytokine is IL-2.

* * * * *